US010822635B2

(12) United States Patent
Akkus et al.

(10) Patent No.: US 10,822,635 B2
(45) Date of Patent: Nov. 3, 2020

(54) METHODS AND DEVICES FOR DIAGNOSIS OF PARTICLES IN BIOLOGICAL FLUIDS

(71) Applicant: CASE WESTERN RESERVE UNIVERSITY, Cleveland, OH (US)

(72) Inventors: Ozan Akkus, Cleveland Heights, OH (US); Mikhail Slipchenko, West Lafayette, IN (US); Anna Akkus, Cleveland Heights, OH (US); Shan Yang, Cleveland Heights, OH (US); Bolan Li, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 111 days.

(21) Appl. No.: 16/111,798

(22) Filed: Aug. 24, 2018

(65) Prior Publication Data
US 2018/0363024 A1 Dec. 20, 2018

Related U.S. Application Data

(62) Division of application No. 14/897,432, filed as application No. PCT/US2014/041863 on Jun. 11, 2014, now Pat. No. 10,059,978.
(Continued)

(51) Int. Cl.
*C12M 1/00* (2006.01)
*C12Q 1/40* (2006.01)
(Continued)

(52) U.S. Cl.
CPC ............... *C12Q 1/40* (2013.01); *C12Q 1/37* (2013.01); *G01N 1/4077* (2013.01); *G01N 21/65* (2013.01);
(Continued)

(58) Field of Classification Search
CPC ..................................... C12M 29/04
See application file for complete search history.

(56) References Cited

U.S. PATENT DOCUMENTS 6,043,216 A 3/2000 Toback et al.
6,654,120 B2 11/2003 Ban
(Continued)

FOREIGN PATENT DOCUMENTS

| WO | 0043777 A1 | 7/2000 |
|---|---|---|
| WO | 2007112449 A2 | 10/2007 |
| WO | 2009134359 A1 | 11/2009 |

OTHER PUBLICATIONS

Cheng et al., Analysis of Crystals Leading to Joint Arthropathies by Raman Spectroscopy: Comparison with Compensated Polarized Imaging, Applied Spectroscopy, Apr. 2009, vol. 63, No. 4, pp. 381-386.

*Primary Examiner* — Rosanne Kosson
(74) *Attorney, Agent, or Firm* — Hudak, Shunk & Farine Co. LPA

(57) ABSTRACT

Methods for determining whether certain compounds, in particular crystals, are present in a sample of a biological fluid that indicates an individual has a particular disease or condition, such as but not limited to gout, pseudogout or urinary tract stones. In some embodiments, the methods include the steps of digestion and filtration of a sample of synovial fluid in order to isolate, if present, monosodium urate monohydrate (MSU), calcium pyrophosphate dihydrate (CPPD), or calcium phosphate crystals from the sample, wherein the filtrate is analyzed with a Raman device to ascertain the presence and type of the crystals. Devices for performing steps of the method are disclosed.

10 Claims, 10 Drawing Sheets

Related U.S. Application Data

(60) Provisional application No. 61/833,688, filed on Jun. 11, 2013.

(51) Int. Cl.
  *G01N 21/65* (2006.01)
  *C12Q 1/37* (2006.01)
  *G01N 1/40* (2006.01)

(52) U.S. Cl.
  CPC .............. *G01N 2001/4088* (2013.01); *G01N 2201/121* (2013.01); *G01N 2333/928* (2013.01); *G01N 2333/958* (2013.01); *G01N 2800/107* (2013.01); *G01N 2800/345* (2013.01)

(56) References Cited

U.S. PATENT DOCUMENTS

| | | |
|---|---|---|
| 8,390,805 B2 | 3/2013 | Kuo et al. |
| 2002/0164651 A1 | 11/2002 | Steinbeck |
| 2003/0164333 A1* | 9/2003 | Nohren, Jr. .......... B01D 63/024 210/650 |
| 2004/0045892 A1 | 3/2004 | De La Cruz |
| 2007/0225668 A1 | 9/2007 | Otto |
| 2010/0042001 A1 | 2/2010 | Ferguson et al. |
| 2010/0284863 A1 | 11/2010 | Downward et al. |

\* cited by examiner

METHODS AND DEVICES FOR DIAGNOSIS OF PARTICLES IN BIOLOGICAL FLUIDS

This invention was made with government support under contract number R01AR057812 awarded by the National Institutes of Health. The government has certain rights in the invention.

FIELD OF THE INVENTION

The present invention relates to methods for determining whether certain compounds, in particular crystals, are present in a sample of a biological fluid that indicates an individual has a particular disease or condition, such as but not limited to gout, pseudogout or urinary tract stones. In some embodiments, the methods include the steps of digestion and filtration of a sample of synovial fluid in order to isolate, if present, monosodium urate monohydrate (MSU), calcium pyrophosphate dihydrate (CPPD), or calcium phosphate crystals from the sample, wherein the filtrate is analyzed with a Raman device to ascertain the presence and type of the crystals. Devices for performing steps of the method are disclosed.

BACKGROUND OF THE INVENTION

Various biological fluids include components such as particulates that can be recovered or extracted therefrom an analyzed in order to determine if an individual possesses a particular condition or disease or precursor thereof.

Gout and Pseudogout

Monosodium urate monohydrate (MSU, leading to gout) and calcium pyrophosphate dihydrate (CPPD, leading to pseudogout) are the most frequently observed crystals types in the joint space. These crystals cause inflammation, pain and destruction in the joint. Gout affects 1-2% of the adult population and its incidence increases with age. Accurate diagnosis of the crystal type is imperative to pursuing correct treatment. A conclusive diagnosis requires the analysis of the synovial fluid aspirates for the presence of crystals.

Gout and pseudogout have very similar symptoms, such as acute and episodic attacks of joint warmth, pain, swelling, and stiffness, thus are often clinically confused with each other. However, the treatment of gout and pseudogout and different because the crystals accumulated are not the same. Therefore, accurate diagnosis is essential for effective treatment of the disease.

Microscopic polarized imaging (PLM), which is presently the clinical standard of identifying pathologic crystals in synovial aspirates of patients with gouty symptoms, has limited sensitivity, and is prone to the subjectivity of the different operators. Currently, false negative rate in gout is 30%, and false positives happen up to 20% of the time has been reported in the literature, lead to inappropriate long-term treatment and delay the treatment of the actual cause. There is a clear need for affordable, automated and portable technologies at the primary care setting for reducing the unacceptably high misdiagnosis rate of crystal species in joint spaces. A lower misdiagnosis would impact patients' quality of life as it translates to less suffering, less deterioration of joints and avoidance of incorrect treatments, introducing cost savings.

Raman spectroscopic analysis of synovial aspirates carries a diagnostic potential. McGill et al identified gout crystals in a synovial smear and a gouty tophus from a limited number of clinical samples using Raman analysis. Maugars et al observed CPPD crystals in cartilage, muscle, and tendon sections using Raman microscopy. Hawi et al have identified cholesterol crystals within cells resident in synovial aspirates. These studies utilized Raman spectroscopy in the microscopy mode which requires seeking for individual crystals visually on a large field of view. This strategy necessitates the utilization of research-grade Raman instruments with premium signal collection capability and, thus, limits the translation of the method to the clinical applications. Recently, sample preparation methods have been developed to congregate crystals at well-defined locations, enabling point-and-shoot Raman spectroscopy at clinically relevant crystal concentrations where the diagnostic performance of Raman analysis compared favorably over PLM in a limited number of clinical samples. Based on this premise, Raman spectroscopy based diagnosis of crystal species in synovial aspirates is beginning to gain feasibility.

Urinary Tract Stones

About 10% of the population develop stones in the urinary tract. Half of patients with kidney stones will have another attack within 5-10 years. If diagnosed correctly and timely, occurrence or recurrence of stones can be treated by diet and/or medications specific to the types of stones which are present. Kidney stone management market size is expected to increase from the current level of $420M to $500M by 2016.

The current paradigm of diagnosis and treatment of kidney stones has a number of unmet needs. First, the stone is not diagnosed until it has formed enough mass to be identified by the imaging studies such as CT scans. Second, the composition of the stone is not identified until and when the stone is removed or passed spontaneously. Third, in majority of modern day surgery, powerful energy sources are used to powder fragments of the stones so the patient could pass them and therefore the fragments of the stone may not be obtained for future analysis. Fourth, there are no available technologies to monitor the status of those patients with high risk of redeveloping stones, or to assess their responsiveness to treatment. Most physicians do not monitor high risk patients due to the absence of a practical diagnostic method that can be executed at the point of care.

Compositional analysis of urinary stones, performed after the confirmation of stone existence, is critical for both effective clinical treatment and recurrent prevention. Imaging modalities such as CT, X-rays and ultrasonography do not provide specific information on the type and composition of stones. Available techniques for stone compositional analysis (e.g. wet chemical analysis, infrared spectroscopy, x-ray diffraction, and scanning electron microscopy) are performed by specialty labs using bulky and expensive equipment. Instrument operation and data interpretation require expert operators. Further, there are indirect costs associated with shipping and handling samples and coordinating the test results post hoc. A technology that would enable compositional diagnosis at the point of care would eliminate such indirect costs and also reduce the number of patient visits.

SUMMARY OF THE INVENTION

In view of the above, one problem of the present invention is to provide methods and devices that can be utilized to determine whether various compounds, such as crystals, are present in a sample of a biological fluid that indicates an individual has a particular disease or condition.

In view of the above, another problem of the present invention is to provide a method that distinguishes between monosodium urate monohydrate and calcium pyrophosphate dihydrate compounds, in the form of crystals, that accurately distinguish between the compounds that cause gout and pseudogout diseases respectively.

Also in view of the above, another problem of the present invention is to provide a method and device for identifying types in amounts of urethral or kidney stones, whether extracted from urine or recovered surgically.

The above mentioned problems as well as other problems known in the art are solved by the methods and devices of the present invention which provide a cost-efficient automated device for diagnosis of crystals in biological fluids, such as blood, urine and synovial aspirates.

A further object of the present invention is to provide an affordable, automated and portable technology that can be utilized in a primary care setting for reducing the unacceptably high misdiagnosis rate of crystal species in joint spaces. A lower misdiagnosis rate would impact patients' quality of life as it translates to less suffering, less deterioration of joints and avoidance of incorrect treatments, introducing cost savings.

Additional objects of the present invention are to provide a method for testing for the presence of biological particles or crystals at a point of care, such as a community based primary care center, home-office, or pathology unit, which can be attained by integrating a cost-efficient automated Raman device.

Yet another object of the present invention is to provide a method that is affordable, automated, and readily available to primary care facilities that can accurately identify pathologic crystals in biological fluids, namely synovial aspirates of patients with gout-like symptoms or urethral or kidney stones in urine samples.

Yet another object of the present invention is to provide a method for determining whether certain compounds, in particular crystals, are present in a sample, in particular a sample of synovial fluid, including the step of performing a digestion step of the fluid which has the effect of releasing, when present, marker compounds or crystals, in particular from an organic material or reducing the viscosity of the fluid.

Yet another object of the present invention is to provide a method that includes the step of filtering a digested sample fluid and further the step of analyzing the filtrate, in particular with a Raman device.

Still another object of the present invention is to provide a method for determining if one or more of the following crystals are present in a sample of synovial fluid: monosodium urate monohydrate (MSU), calcium pyrophosphate dihydrate (CPPD), hydroxyapatite (HA), octacalcium phosphate (OCP), tricalcium phosphate (TCP), calcium oxalate (CO), cystine and xanthine; all of which are Raman active.

A further object of the present invention is to provide a filtration device desirable for congregating crystals in a preferred area.

Accordingly, one aspect of the present invention is a method for diagnosing for one or more of kidney stones, gout and pseudogout, comprising the steps of: obtaining a sample of urine or synovial fluid; performing digestion of the fluid to release crystals or particles in the fluid; filtering the digested fluid to recover the released crystals or the particles; and analyzing the crystals or the particles with a diagnostic device, and determining if gout-causing or pseudogout-causing crystals or the particles are present.

In another aspect of the invention, a filter cartridge for collecting crystals from a fluid is disclosed, comprising a filter holder having a base including an outlet and a top including an inlet; a condensing piece located within the filter holder and having an inlet and an outlet, with the outlet in fluid communication with the filter base; and a filter membrane located between the condensing piece and the filter holder top, wherein the condensing piece channels flow of a fluid through the filter membrane such that a filtrate is collected at a location on the filter membrane that is smaller than a total surface area of the filter membrane.

Another aspect of the invention is a method for determining if a particle or crystal is present in a sample of biological fluid, comprising the steps of obtaining a sample of a biological fluid; filtering the biological fluid to recover particles or crystals in a filter cartridge; and analyzing the crystals with a Raman device and determining if the particles or the crystals are present, wherein the Raman system includes a receptacle adapted to receive the filter cartridge containing the filtrate.

BRIEF DESCRIPTION OF THE DRAWINGS

The invention will be better understood and other features and advantages will become apparent by reading the detailed description of the invention, taken together with the drawings, wherein.

DETAILED DESCRIPTION OF THE INVENTION

Figure 1:
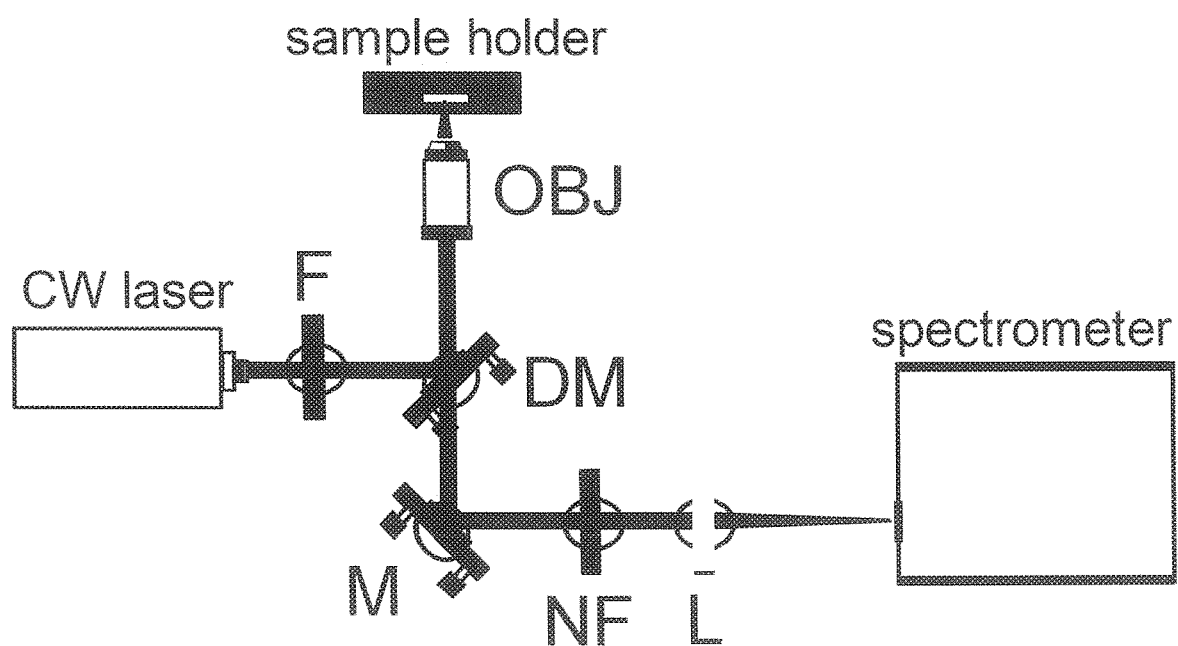
FIG. 1 is a schematic diagram of the optical layout and basic components of the low-fidelity custom Raman set-up. The components included F: laser line filter, DM: dichroic mirror, OBJ: objective lens, M: mirror, NF: notch filter, L: lens, sample holder and spectrometer.

Methods for clinically diagnosing the presence of a disease or condition such as, one or more of presence of kidney stones, gout and pseudogout, in a sample of a biological fluid, such as synovial fluid, blood and urine, are disclosed. Devices, in particular, Raman-based testing devices are also provided for use in performing the methods of the invention.

The methods of the present invention in some embodiments include a sample supplementation or digestion step and a filtration step that isolate desired compounds, namely crystals, from synovial fluid while reducing the fluorescence organic burden.

Sample Collection

The method of the invention involves collection of fluid from a desired subject. In order to test for presence of diseases such as gout and pseudogout, synovial fluid is obtained from the subject. Synovial fluid collection is well known to those of ordinary skill in the art. Blood and urine collection is also well known to those of ordinary skill in the art.

Sample Supplementation

The synovial fluid sample obtained is further processed prior to analysis. In one embodiment, the fluid is supplemented with a compound that is adapted to at least partially release the crystals or compounds from organic debris present in the sample and to reduce the viscosity of the synovial fluid for ease of filtration. The clinically retrieved synovial fluids are digested first with a glycosaminoglycan-cleaving enzyme and second with a protein-cleaving enzyme. In one embodiment the glycosaminoglycan-cleaving enzyme is hyaluronidase. In a preferred embodiment, the protein cleaving enzyme is, for example, proteinase-K. Other suitable compounds that can be added to the fluid include, but are not limited to, collagenase, gelatinase, papain, pepsin and amylase. The supplementation processes are also known in the art as digestion. In some embodiments it is desirable to supplement the synovial fluid with a detergent, especially when lipids are present. The detergent can be added prior to adding the glycosaminoglycan-cleaving enzyme or after, or even after the protein-cleaving enzyme is added to the synovial fluid.

In one embodiment, suitable amounts of the desired glycosaminoglycan- and protein-cleaving enzymes are, for example about 0.5 mg/ml of the hyaluronidase and about 1 mg/ml of proteinase-K. Depending on the enzymes utilized, the concentration ranges can be lower or higher, such as, but not limited to 0.05 mg/ml to 10 mg/ml. In one embodiment, a detergent is Triton X100. Treatment times are sufficient to release the desired crystals or compounds when present. For example, in one embodiment the glycosaminoglycan-cleaving enzyme is allowed to proceed from about 1 to about 30 minutes and preferably for about 15 minutes prior to adding the protein-cleaving enzyme, which is then allowed to digest proteins for about 1 to about 90 minutes, and preferably for about 45 minutes. Detergent treatment can last from about 1 to about 20 minutes and preferably for about 5 minutes, when utilized.

Filtration

The supplemented fluids are then filtered to recover a filtrate, after a suitable period of processing time, which is generally from substantially no wait time up to about 2 hours in one embodiment.

Figure 10:
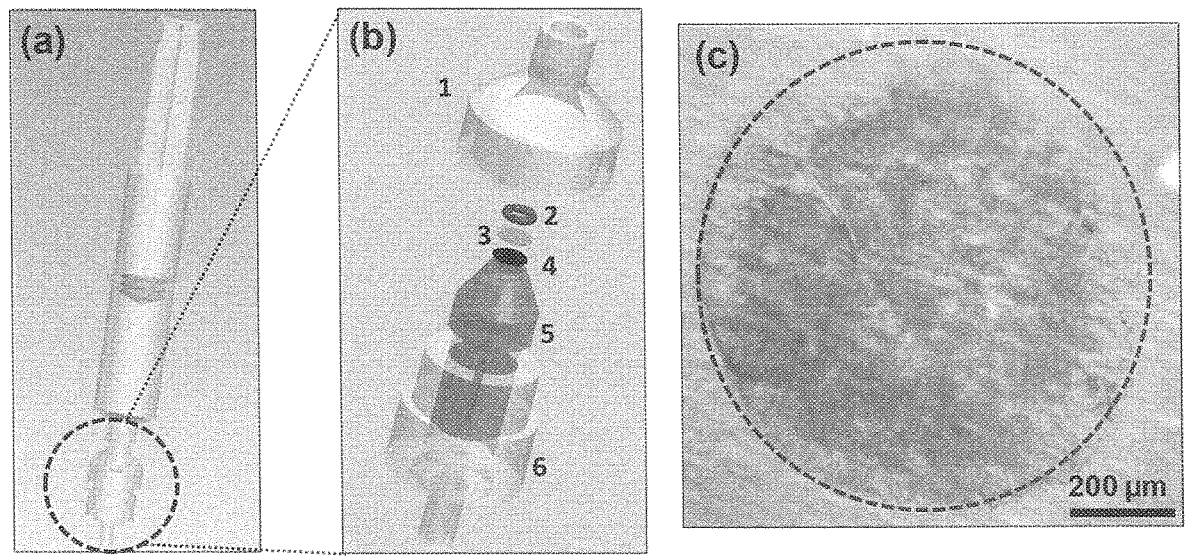
FIG. 10 illustrates (a) digested synovial fluid transferred into a regular syringe mounted with a custom filtration cartridge; (b) Design of a filtration cartridge composed of components of a standard filter holder (1,6), an o-ring (2), a filter membrane (3), an aluminum foil disc (4), and an epoxy casting piece (5); (c) Microscopic image of MSU crystals deposited at the center of the membrane.

In one embodiment, a filter cartridge is specifically designed to guide and constrict the flow of fluid to a spot on the filter wherein desired compounds, preferably the crystals, to be analyzed are captured. One embodiment of a filter cartridge is shown in FIG. 10(*b*). The filter includes a two-piece housing or holder having a top 1 and a base 6, the top including an inlet and the base including an outlet. A filter membrane 3 is captured within the filter holder. An o-ring 2 is utilized in some embodiments and placed in the filter holder top 1 such that the fluid can flow through the aperture in o-ring 2. The filter membrane 3 lies against o-ring 3 on one side and a disc 4 also including an aperture on the opposite side, the disc also including an aperture for fluid flow. In one embodiment, the disc is a metal disc, such as formed from aluminum. The purpose of the disc is to block interference from the condensing piece which also limits the fluid flow to the center portion of the filter membrane 3. In one embodiment, the condensing piece is cast epoxy. The condensing piece was formed as described herein, directly on the base portion of the filter holder, the condensing piece including a fluid passage to receive fluid passed through the filter membrane 3. In other embodiments, the filter cartridge can be formed from three pieces, namely two housing pieces and a filter membrane which is captured therebetween. In one embodiment, the fluid mixture can be drawn or placed into a syringe which is then fitted with the filter cartridge including the filter, for example a one micrometer filter available from Millipore, whereafter the fluid is filtered to retain the filtrate, for examples crystals which are subsequently analyzed. One can supplement the solution with ions such as calcium, phosphate, sodium, uric acid etc. to prevent the crystals from dissolving. Various embodiments of filter holders are described herein. One can use a filter from 0.01 or 0.1 microns to 500 microns depending on particulate size. In one embodiment, the filter membrane is polytetrafluoroethylene or a polyolefin such as polypropylene.

As described herein, the filter cartridge of the invention collects the sample to be measured at a particular spot so that rapid analysis can be performed by the Raman device. That said, in various embodiments, the filter cartridge retains particulates or crystals over a spot having a diameter less than 3 mm, desirably less than 2 mm and preferably less than 1 mm. Following filtration, the filter cartridge is transferred directly to the Raman device and the crystals are particulates captured thereby are analyzed.

Analysis

The filter holder is removed and placed in a Raman device for diagnosis. The spectral data obtained from the Raman device is analyzed in order to determine whether crystals or other target particulates are present, such as gout-causing or pseudogout-causing crystals or urethral or kidney stones, so that the subject can be treated as appropriate.

EXAMPLES

Set A

Sample Collection and Preparation

Synovial aspirates were collected from seven patients presenting "gout-like symptoms" and three asymptomatic synovial aspirates obtained from Anatomy Gifts Registry (Hanover, Md.) where the donors did not have any known joint disease history. Symptomatic sample collection was conducted under the approvals of Institutional Review Boards of institutions where synovial samples were collected (Metro Health Hospital, Cleveland, Ohio and Henry Ford Hospital, Detroit, Mich.). The patients presented to the clinic with gout-like symptoms and aspirates were collected as part of the normal diagnostic procedure. Symptomatic samples had aggregates within the fluid whereas the asymptomatic samples were clear in appearance. The synovial fluid samples were frozen following collection and kept frozen during shipment and long-term storage at −20° C. The presence of MSU crystals were confirmed by compensated polarized imaging as known in the art.

Synovial fluid samples were digested with glycosaminoglycan-and protein-cleaving enzymes (hyaluronidase at 0.5 mg/ml and proteinase-K at 1 mg/ml, Sigma-Aldrich) to release the crystals from the organic debris and also to reduce the viscosity of synovial fluid for ease of filtration. The digested synovial fluids were transferred to a syringe and filtered through a custom-made filter cartridge mounted at the syringe tip. The filter cartridge was designed to guide and constrict the flow to a spot of polypropylene filter (30 μm, EMD Millipore, Billerica, MA), retaining crystals over a 0.7 mm diameter spot for the later Raman analysis. In other embodiments, the size can range from 0.1 mm to 10 mm. The presence of MSU crystals obtained from clinical samples (needle-like, 2~20 μm in length) at the filtration site was confirmed by SEM at a magnification of 2500×.

Synthetic MSU crystals were prepared following earlier protocols which yield crystals with similar size, morphology and birefringence to those found in gout and pseudogout, as confirmed by compensated polarized imaging and X-ray diffraction earlier. Raman spectra were acquired from pure synthetic crystals to be used as reference for clinically obtained MSU crystals.

Raman Spectroscopy

Raman analyses of samples were carried out by using custom-made Raman set-ups on an optical bench using interchangeable components to accommodate analysis at multiple wavelengths. The Raman shift measured by the systems was calibrated using the 520.7 $cm^{-1}$ peak of a Si wafer. MSU crystals were identified by their characteristic peak at 631 $cm^{-1}$ which originates from the vibrations of the purine ring. Spectra of unfiltered, pure components were also acquired in powder form to confirm peak locations.

In order to compare the Raman fluorescence levels from asymptomatic and symptomatic synovial fluids, three asymptomatic and three symptomatic filtration samples were investigated with the above 785 nm system. The background fluorescence at 650 $cm^{-1}$ was recorded at three randomly picked points in each filtration spot for each sample. The 650 $cm^{-1}$ was selected mainly because it constitutes the baseline of the major MSU peak located at 631 $cm^{-1}$. Mann-Whitney U Test was applied to test the differences between the two groups and the level of significance was set as $P<0.05$.

Results

Figure 4:
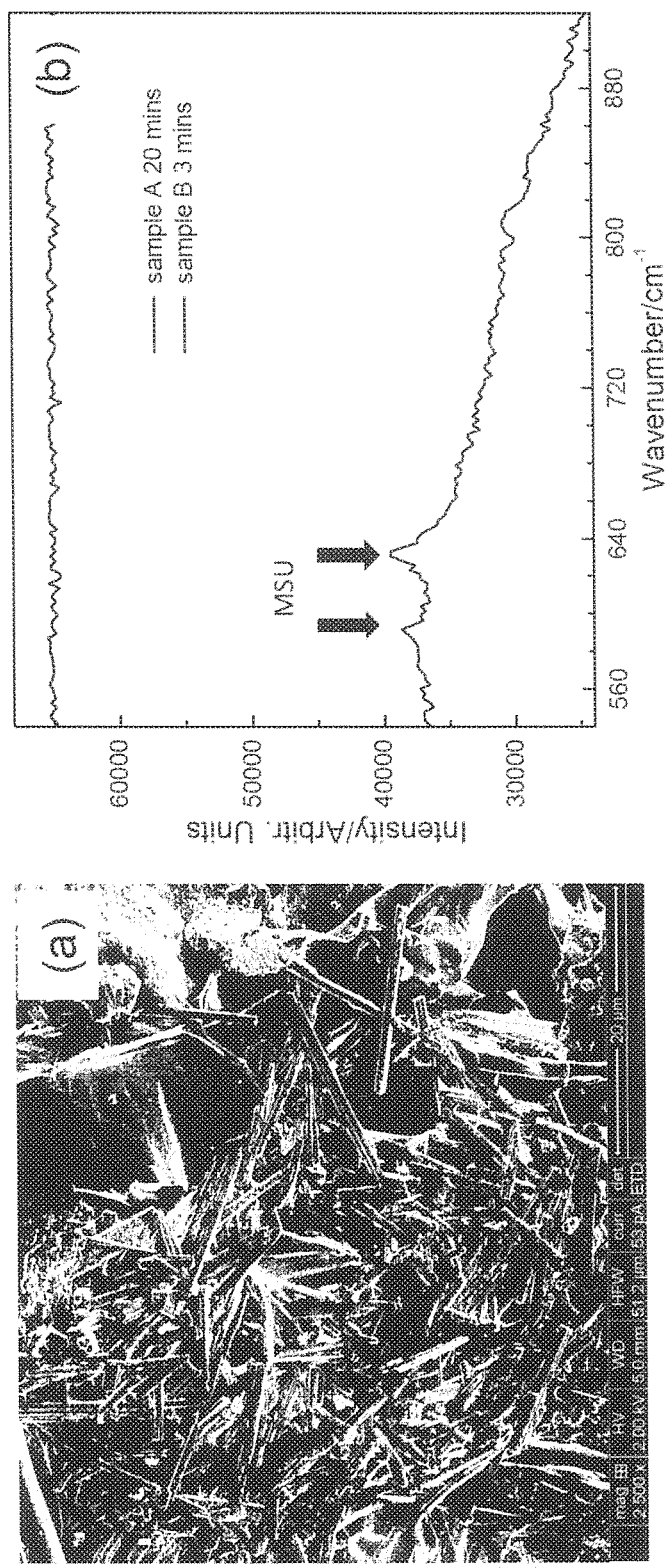
FIG. 4 illustrates (a) SEM image of MSU crystals isolated from a clinical sample deposited on filter (×2, 500 magnification); (b) Representative Raman spectra from a highly fluorescent symptomatic MSU sample recorded by the custom Raman setup at 690 nm (25 mW, signal integration time 6 seconds, no averages), after 3 minutes and 20 minutes of photobleaching, respectively. Red arrows indicate the signature MSU peaks.

SEM images of MSU crystals filtered from synovial fluid using the filtration device confirmed the presence of needle-shaped crystals at the filtration deposit site (FIG. 4a). Raman spectra were collected at such deposits at 532, 660, 690 and 785 nm. The BF prevented any measurements to be performed at 532 nm, regardless of the duration of photobleaching. Raman spectra collected at 660 nm excitation from filtered symptomatic samples displayed substantial amount of BF at the baseline which saturated the CCD. However, following 5-10 minutes of photobleaching, it was possible to collect spectra at 660 nm. At 690 nm, Raman spectra from most samples could be acquired after 3 to 5 minutes of photobleaching after which MSU peaks could be observed (FIG. 4b, lower trace). Nevertheless, there were a few highly fluorescent samples from which the signal saturated the CCD even after 20 minutes of photobleaching (FIG. 4b, top trace).

Figure 5:
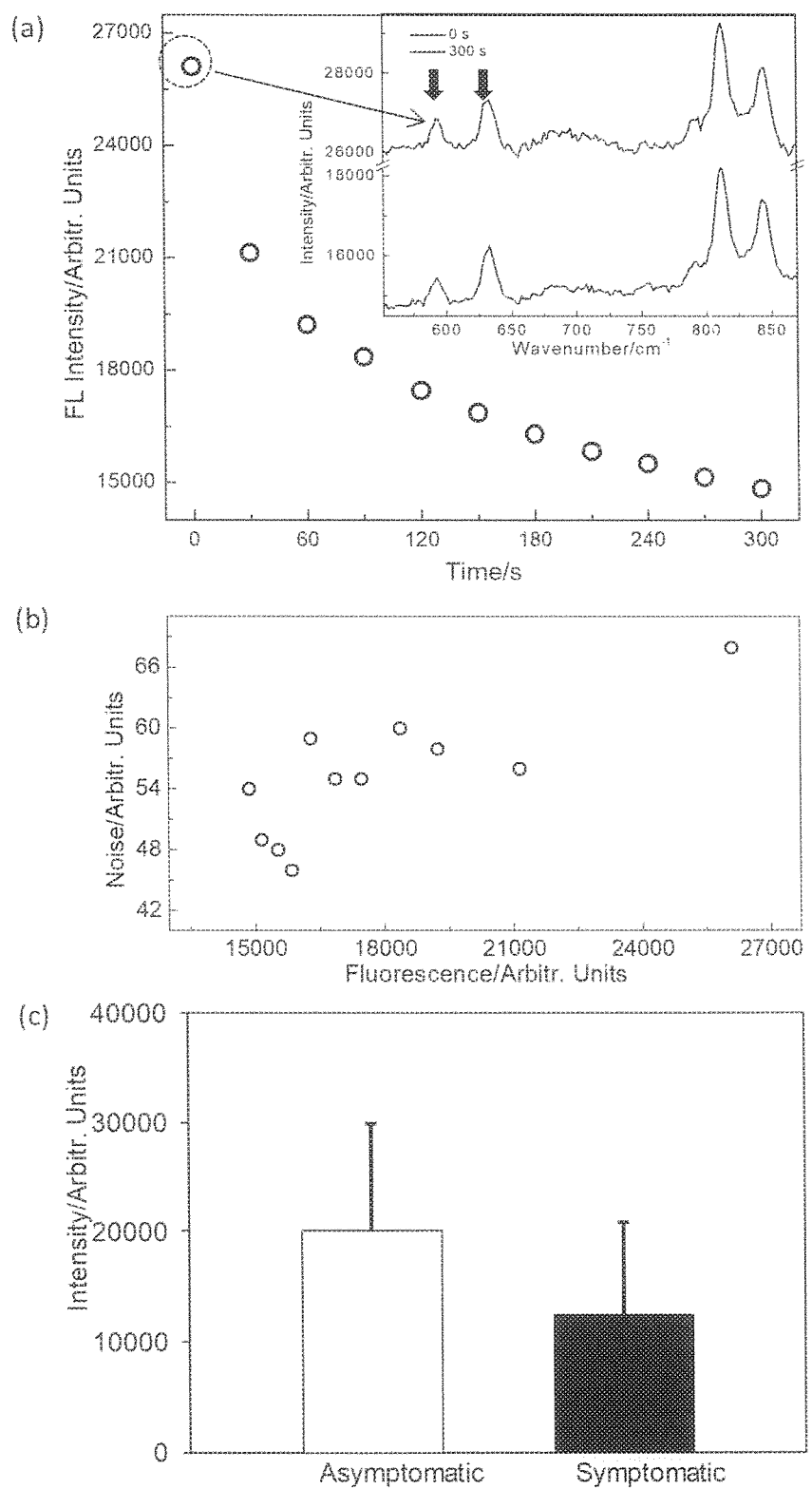
FIG. 5 illustrates dependence of fluorescence on time (a) and noise level dependence on fluorescence (b) of synovial fluid deposited on a filter measured by the OEM Raman system at 785 nm (integration time 0.5 s, laser power 60 mW). The noise level is determined by the standard deviation of the peak-free region at 680-740 $cm^{-1}$ following the baseline correction. The inset in (a) showed the spectra corresponding to the first and the last data points in the main plot. (c) Background fluorescence intensities at 650 $cm^{-1}$ for asymptomatic and symptomatic samples.
Figure 6:
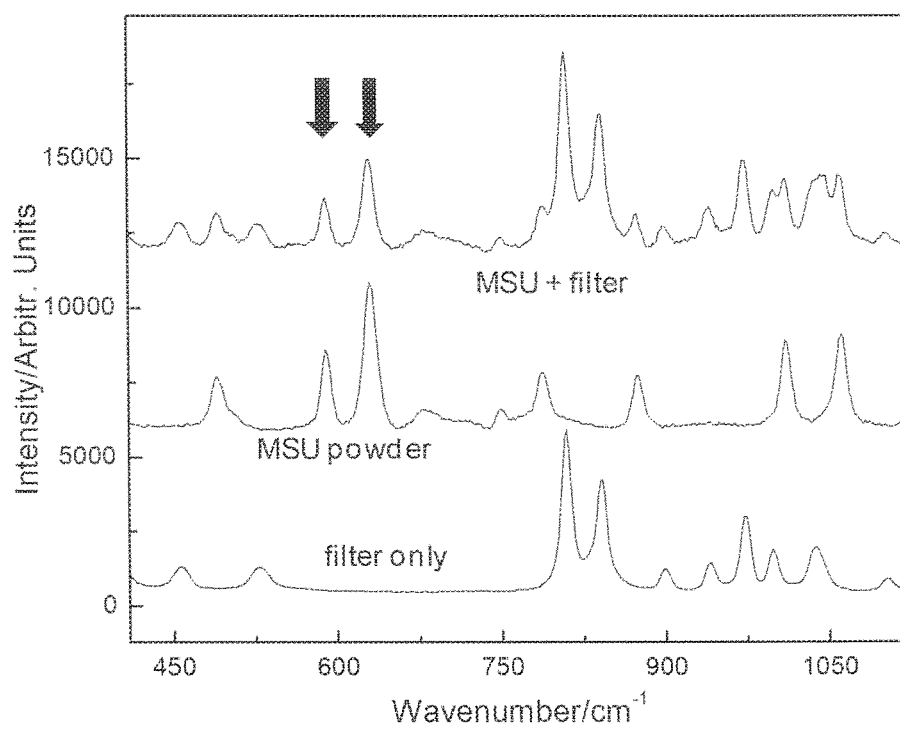
FIG. 6 illustrates Representative Raman spectra of clinical MSU crystals deposited on polypropylene filter, as well as pure MSU crystals and a clean filter. Spectra were recorded by the OEM Raman setup with 785 nm excitation. The spectra were vertically shifted following BF correction for better viewing. The laser power was 60 mW and the integration time was 1 second and averaged 10 times.

Background fluorescence was present at 785 nm excitation as well; however, it was not prohibitive as it was the case for the shorter wavelengths. For samples with the strongest fluorescence, the Raman spectrum with identifiable MSU peaks could be recorded immediately after the laser light was delivered to the sample using shorter integration times (0.5 s) (FIG. 5a inset). Spectral data demonstrated a reduction in fluorescence after it was continuously illuminated with the laser light. The intensity of BF decayed exponentially with the photobleaching time for 785 nm (FIG. 5a). An increase of spectral noise was observed with higher BF level (FIG. 5b). Therefore, higher signal to noise ratio may be obtained by recording Raman spectrum after photobleaching the sample for a short duration (~1 min). The signal intensity of the MSU peak did not change with the level of fluorescence. The background fluorescence intensities in Raman spectra collected at 785 nm from asymptomatic samples were significantly greater than symptomatic samples (FIG. 5c) ($P<0.05$).

The Raman shifts at 590 and 631 $cm^{-1}$ representing signature peaks of MSU crystals were evident in spectra of clinical and standard samples collected by the higher-fidelity system over 1 second signal collection time and with no photobleaching. The spectral peaks of the filter material did not overlap with the peaks of interest of MSU.

Discussion

The example testing investigated the fluorescence from asymptomatic and symptomatic synovial aspirates in the context of Raman-based diagnosis of crystals leading to arthritic symptoms in the joint space. Following a digestion and custom filtration process, crystals were extracted from synovial aspirates and collected over submillimeter spots for point-and-shoot Raman spectroscopy. Digestion was desirable and preferable for several purposes. First, the organic debris/aggregates included crystals which were released to the fluid after digestion, increasing the recovery efficiency of crystals. Second, the hyaluronic acid phase imparts viscosity to the synovial fluid which in turn makes syringe filtration hard. Digestion of the hyaluronic acid was observed to decrease the viscosity and allow filtration. Fluorescence and absorbance was conducted before and after digestion to assess whether the addition of enzymes affected the absorbance/fluorescence profiles.

Synovial fluid is a complex mixture that contains water, hyaluronic acid, ions, proteins, and cells. Physiologically normal synovial fluid is transparent and clean. The composition of synovial fluid from symptomatic patients is much more complex due to inflammatory processes and overabundance of cells. The appearance of symptomatic synovial fluid is frequently turbid with presence of organic aggregates and, occasionally blood.

Figure 2:
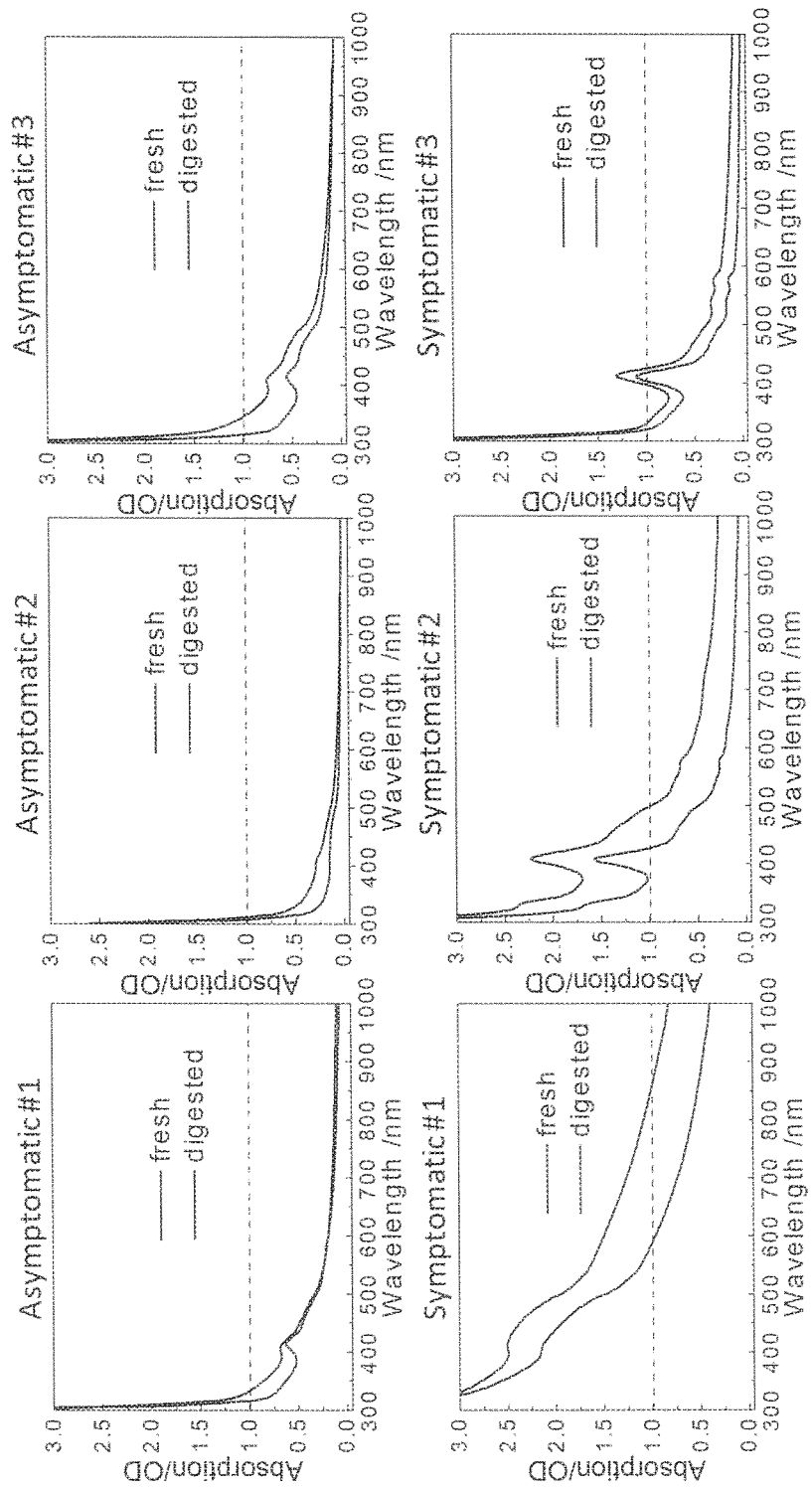
FIG. 2 is an absorbance spectra of synovial fluids. Data were taken from as-retrieved synovial fluids collected from asymptomatic and symptomatic patients, also, before and after digestion.

Enzymatic digestion of samples resulted in slightly increased absorbance in asymptomatic samples whereas absorbance in symptomatic samples decreased notably following digestion (FIG. 2). Particulate aggregates in the symptomatic synovial fluid were cleaved into smaller pieces by digestion which may have attenuated the scattering effects and led to an overall decrease of absorbance profile for symptomatic synovial fluid. The observed increase of absorbance in asymptomatic fluids following the digestion is unclear. Since asymptomatic fluid lacks organic debris and dominated by hyaluronic acid, it appears that the digestion of hyaluronic acid changes the conformation and size of this glycosaminoglycan in a fashion to increase scattering, and thus, the measured absorbance. Regardless of the dichotomy on the effects of digestion on absorbance of symptomatic versus asymptomatic samples, fluorescence in 500 nm to 600 nm range was reduced in all asymptomatic and one symptomatic samples following digestion (see FIG. 3a).

Although digestion and filtration dissolves and reduces the organic debris burden, there is an unpredicted amount left on the filtrated spot including MSU crystals. The organic debris burden is greater in symptomatic fluid than in asymptomatic fluid to the extent that the former is clear and the latter has visible particulate debris. Based on this difference, one would expect a greater level of fluorescence from symptomatic fluid than from asymptomatic fluid. In contrast to this expectation, fluids from symptomatic patients tended to have lower fluorescence as observed by fluorescence spectra and Raman spectra. Based on this observation, it appears that the fluorescence is not driven as intensely by the organic debris observed in fluid collected from diseased joint. Rather, it appears that the hyaluronic acid that is more prominent in asymptomatic fluid is a contributor to fluorescence and that hyaluronic acid may exist in lower amounts and/or in a different conformation in symptomatic samples to an extent that results in lower fluorescence.

Figure 3:
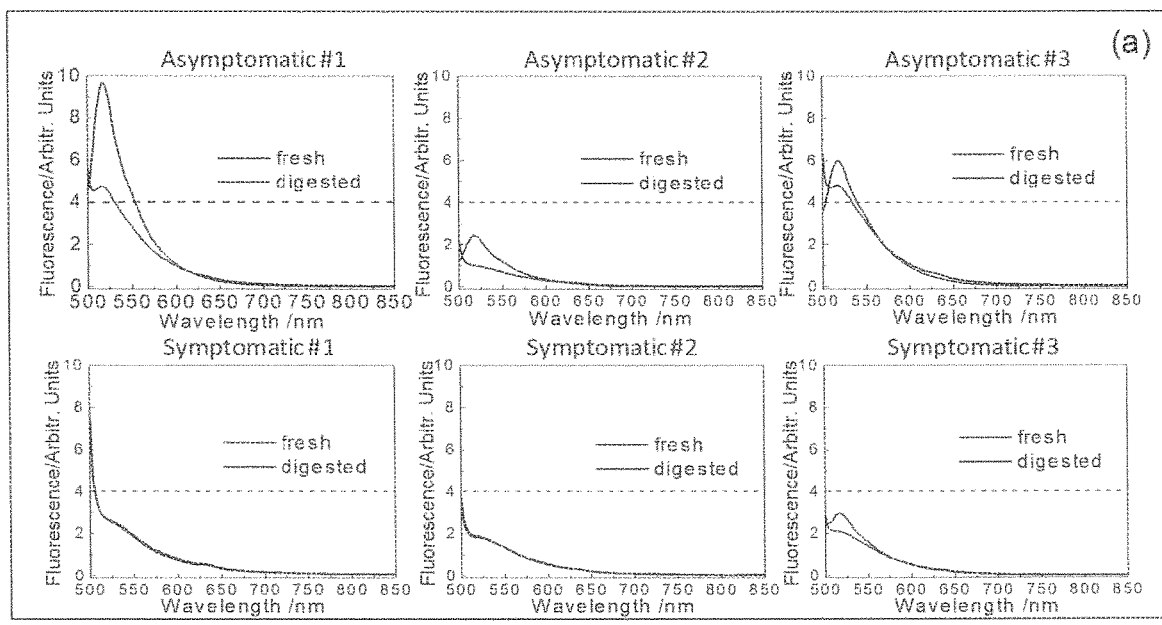
FIG. 3 illustrates (a) Corresponding fluorescence spectra of the samples in FIG. 2, with excitation wavelength set at 475 nm; (b) Images of symptomatic synovial fluid deposited on a filter from a laser scanning confocal microscope, with the emission window set at 500-600, 600-700 nm, and 700-800 nm, respectively.
Figure 3:
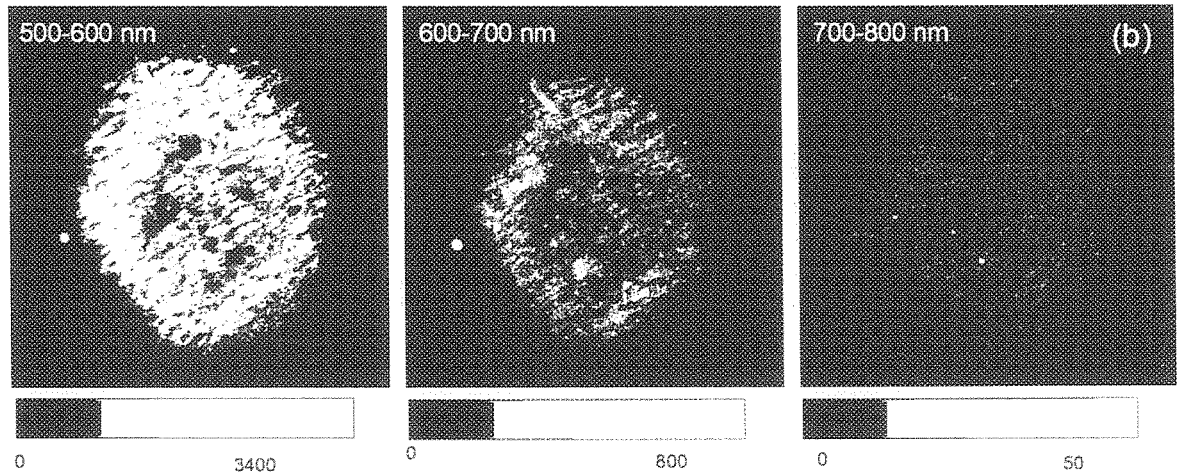

The results shown in FIGS. 3a and 3b suggested that fluorescence interference on Raman spectroscopy of synovial fluid may be overcome by using excitation wavelength longer than 660 nm. For this reason, we investigated Raman system for synovial fluids based on lasers at 660 nm, 690 nm, and 785 nm, aiming to find a compromise between high spectral response at shorter wavelength and less fluorescence at longer wavelength. Results showed that, at 690 nm excitation, for most clinical samples prepared following our protocol, the fluorescence has been reduced to a level that enabled the collection of Raman spectral data with less than 5 minutes of photobleaching (FIG. 4b). However, several samples still displayed extremely strong fluorescence that saturated the spectrometer that did not bleach at durations too lengthy for practical clinical application. Therefore, utilization of lasers at greater wavelengths than 690 nm is advisable.

Raman spectrum can be successfully observed at all samples when 785 nm NIR laser light was used as the excitation source. The range of 700 nm-785 nm can also be utilized. It may be possible that a wavelength in this range may address the fluorescence while providing more signal than 785 nm. However, since 785 nm has become a standard wavelength in Raman analysis, optical components are more readily available, making 785 nm more attractive as a candidate towards integration of a diagnostic device.

Conclusion

The examples demonstrated that filtering of the samples following enzymatic digestion allows the utilization of a Raman device. In addition, we show that the Raman signal can be recovered from crystals at 785 nm laser excitation without being masked by background fluorescence from the organic phase. Given that Raman-based diagnosis is definitive and that it is objective, the method developed can be applied as a point of care convenient diagnostic tool.

Set B

Sample Preparation

Synovial fluid was serially digested to reduce the viscosity and to release the crystals from the organic debris for ease of following filtration, as described herein. One milliliter synovial fluid was loaded in a glass tube and 0.5 mg lyophilized hyaluronidase powder (Sigma, H3506) was added. After 15 minutes digestion at room temperature, the fluid was added with 1 mg Proteinase K (Sigma, P2308), and kept at 37° C. for another 45 minutes The final digested synovial fluid was transferred to a 5 mL regular syringe with a custom-made filter cartridge mounted at the tip.

The cartridge was remodified from a 13 mm standard filter holder (Swinnex, Millipore), by mainly introducing an epoxy casting piece. A regular syringe was inserted into an assembled filter holder in which the underdrain disc had been removed. Then, the prepared mixture of epoxy resin (Buehler, 20-8136-128) and hardener (Buehler, 20-8138-032) was injected into the inner cavity of the holder from the outlet port. The epoxy casting piece was made after overnight curing, with a socket (~3.5 mm diameter, ~4 mm in depth) at the top for the position of the o-ring and the filter membrane. The socket was generated by the extrusion of the syringe tip from the inside of the holder during the casting. Certain milling had to be applied to flatten the rugged surface due to the casting, and a 0.9 mm hole was fabricated at the center of the socket, serving as the channel for the flow.

Instead of dispersing crystals over 13 mm disc (the original design), the custom cartridge was able to guide and constrict the flow of the synovial fluid to go through a small area, retaining crystals over a 0.9 mm diameter spot. The filtration was performed by pushing the digested synovial fluid through a polypropylene membrane (30 μm, EMD Millipore, Billerica, Mass.) filter, where the crystals were retained. The o-ring worked to seal the flow and an aluminum foil disc was positioned between the epoxy casting piece and the filter membrane to remove background Raman peaks coming from the epoxy.

Cost-Efficient Automated Raman Spectroscopy

Following filtration of the biological fluid, the filter cartridge was inserted into a cost-efficient automated Raman device (CARD) designed for diagnosis of crystal species (FIG. 7a). CARD included four major units (FIG. 7a): a receptacle for insertion of the filter cartridge that is mounted on a translation stage; a controller, such as; a micro-controller (Arduino Nano) controlled servo motor (Hitec, HS-785HB) to move the translation stage; an OEM-Raman system (785L, Wasatch Photonics, NC) at 785 nm; and a microprocessor, such as a laptop computer for control and data acquisition. The receptacle is designed such that it is complimentary to the dimensions of filter cartridge. In this manner, the filtrate is positioned at the focal point of the Raman device, see FIG. 7(b) for example. With the system of the present invention including the filter cartridge and Raman device, one does not need to search around a filter member in order to find and then identify the sample. With the methods and devices of the present invention there is no search necessary as the filter cartridge holder of the receptacle positions the filtrate accurately with respect to the laser of the Raman device. Both the 785L system and the servo motor were controlled by the LabVIEW program via USB connection. The mechanical design ensured that the crystal deposited spot was positioned at the focal plane. The device was programmed to acquire spectra from a plurality of, for example at least 2, at least 3, at least 4 or 5, or for example 30 different points at ~30 µm step size along the center diameter of the spot to increase the area surveyed for crystal presence. The Raman spectrum acquired at each point was processed to: 1) remove fluorescence background, 2) subtract the filter related peaks, 3) identify the species based on the detection of peaks associated with MSU crystals at 590 and 631 $cm^{-1}$, etc. Subtraction of filter peaks was executed by normalizing the spectra with respect to 809 cm-1, a wavenumber where MSU spectrum is silent and where the most prominent filter peak is present. The processing and the decision processes were unsupervised and automated in LabVIEW. Synthetic pure MSU crystals were used as reference spectra and to assess system performance. A similar procedure as described above was also used for CPPD crystals.

Raman Mapping

The spectroscopic mapping was conducted using a commercial Raman system (Labram HR800, Horiba Jobin Yvon, Edison, N.J.), to investigate the distribution of crystals deposited on the membrane. The system is composed of a laser source at 785 nm, and measurements were performed using a 1200 lines/mm grating, which provided a spectral dispersion of 1.25 pixels/$cm^{-1}$. The system is equipped with a three-dimension micromotion platform, which allows the laser scanning the entire submillimeter spot. The Raman wavenumber shift measured by the system was calibrated using the 520.7 cm-1 peak of a Si wafer.

The chemical image map was recorded from a clinical crystals deposit over a disc with 1 mm diameter using a X10 objective (Olympus). The laser power at the objective aperture was set at 30 mW, which had been verified as the "safe capacity" (MSU is explosive because of its urate ingredient) for excitation. The 2D map had 30 µm step size along both axes, resulting in collection of 900 spectra. Each spectrum was obtained as the average of 2 consecutive spectra each collected for 4 seconds each. Chemical image was reconstructed based on the intensity of the characteristic peaks of crystals (MSU: 631 $cm^{-1}$, CPPD: 1050 $cm^{-1}$). Raw spectra were filtered and background subtraction was performed using commercial software (Labspec v5, Horiba Jobin-Yvon, Edison, N.J.).

Limit of Detection (LOD)

MSU crystals were suspended in urate PBS buffer at seven different concentrations of 1, 2.5, 5, 10, 20, 50, 100 µg/mL. Urate supplementation was essential to prevent MSU crystals from dissolving and it was confirmed that urate concentrations greater than 5 mg/mL prevented such dissolution as confirmed by microscopic observations of crystals at durations for up to 48 hours (Olympus BX 51). One milliliter of each solution was pushed through the filter cartridge to retain certain amount of crystals on the membrane for Raman spectroscopy. Thirty points were predefined along the horizontal diameter with the step of 30 µm (FIG. 8), and the laser was focused at these points by synchronizing the spectra acquisition and motorization of the cartridge in CARD. CPPD crystals were treated in a similar procedure; however, the aqueous solution was supplemented with calcium to prevent dissolution.

MSU crystals were identified by their 631 $cm^{-1}$ characteristic Raman peak, which originates from the vibration of purine ring, whereas, CPPD crystals were identified from the peak at 1050 $cm^{-1}$ originating from the P-O stretch. To obtain a Raman-based criterion for the amount of crystals, the summation of Raman intensity at these peaks was taken over the thirty points. Naturally, samples with higher concentration led to the presence of crystals at a greater number of points and at greater density per point, which generated greater summation value. Each sample was measured three times as the cartridge was rotated at three random angles, and the outcome was set as the average of the summations taken from the three diameters. The outcome of each sample was plotted against the known concentration of MSU and CPPD separately, to find out the relationship between the two. The significance of the linear regression was determined at the level of P<0.05.

Results

Figure 9:
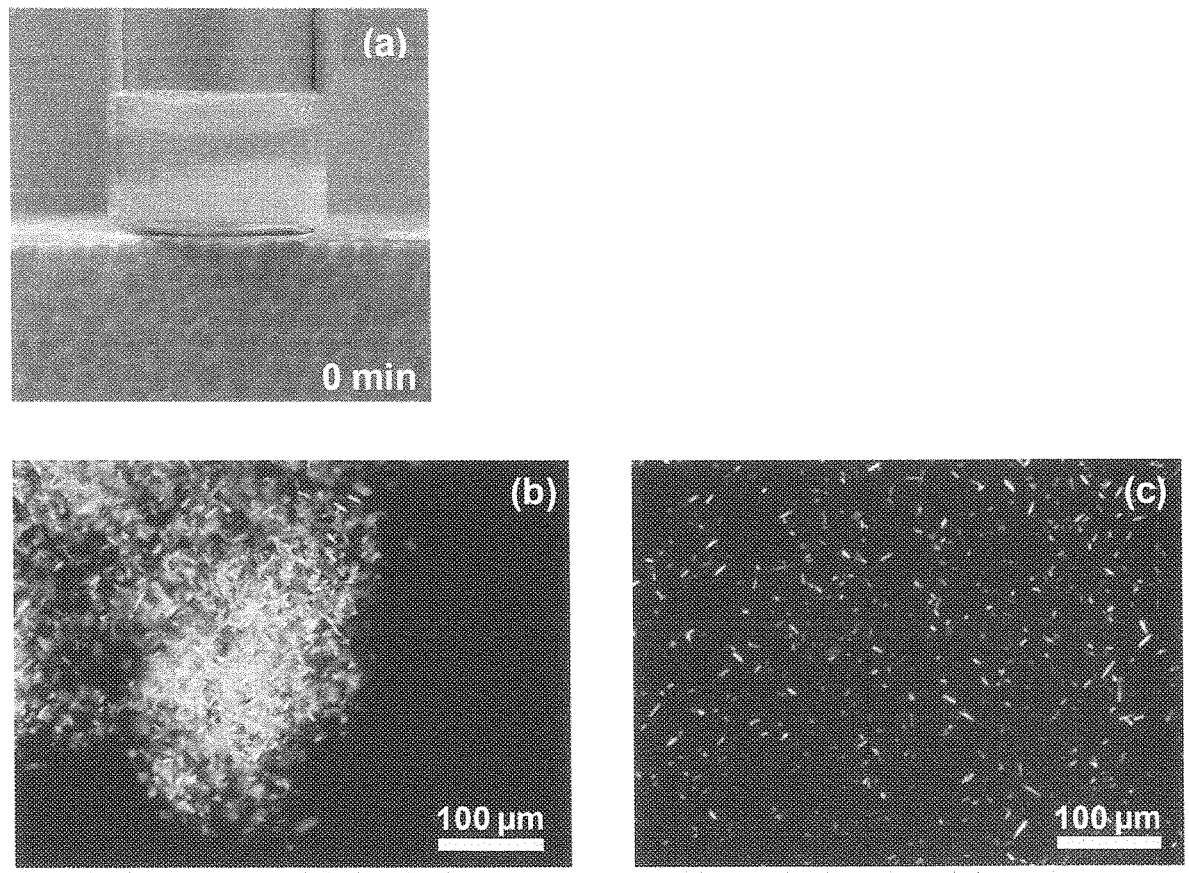
FIG. 9 presents images illustrating (a) organic debris was gradually dissolved by digestion; (b) Before digestion, crystals were aggregated into debris; (c) After digestion, crystals were uniformly released into synovial fluid.

In the absence of digestion, synovial fluid could not be pushed through the filter. However, the filtration and successful isolation of crystals became possible following the digestion. Organic debris was observed to be dissolved by enzymes (FIGS. 9(a)-(c)). The overall treatment time of digestion was ~90 minutes.

Figure 11:
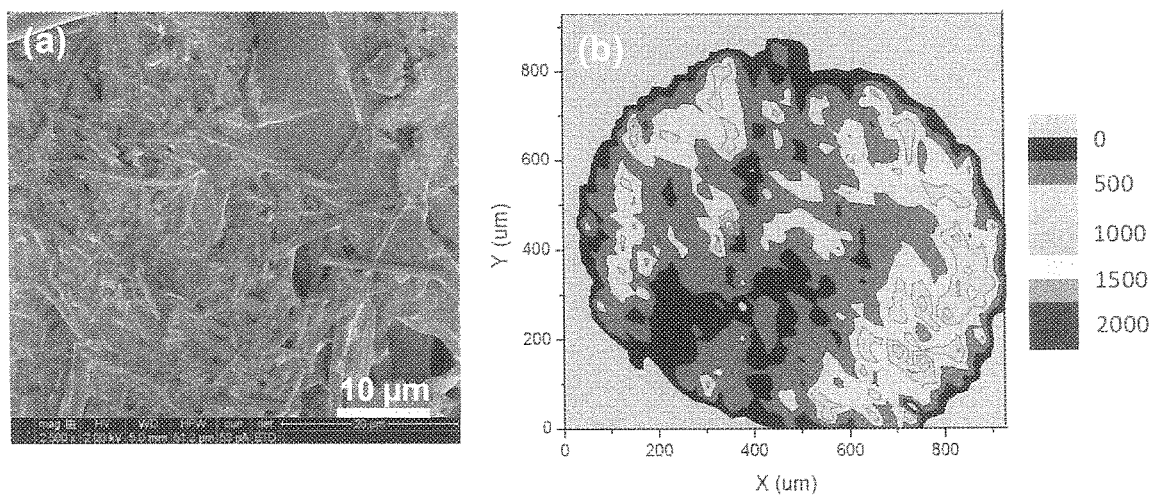
FIG. 11 illustrates (a) SEM image of MSU crystals (needle shape) retained on the filter membrane in the cartridge; (b) Raman mapping image showed the distribution of crystals over the submillimeter spot.

In the custom filter cartridge, crystals were deposited on the membrane in a spot with the diameter of ~900 µm (FIGS. 10(a)-(c)), and the presence of clinical MSU crystals at the filtration site was confirmed by SEM at a magnification of 2500× (FIG. 11(a)). The distribution of clinical MSU crystals in the deposition was examined by chemical image-map (at 631 $cm^{-1}$) generated by the research-grade Raman system (FIG. 11(b)).

Figure 7:
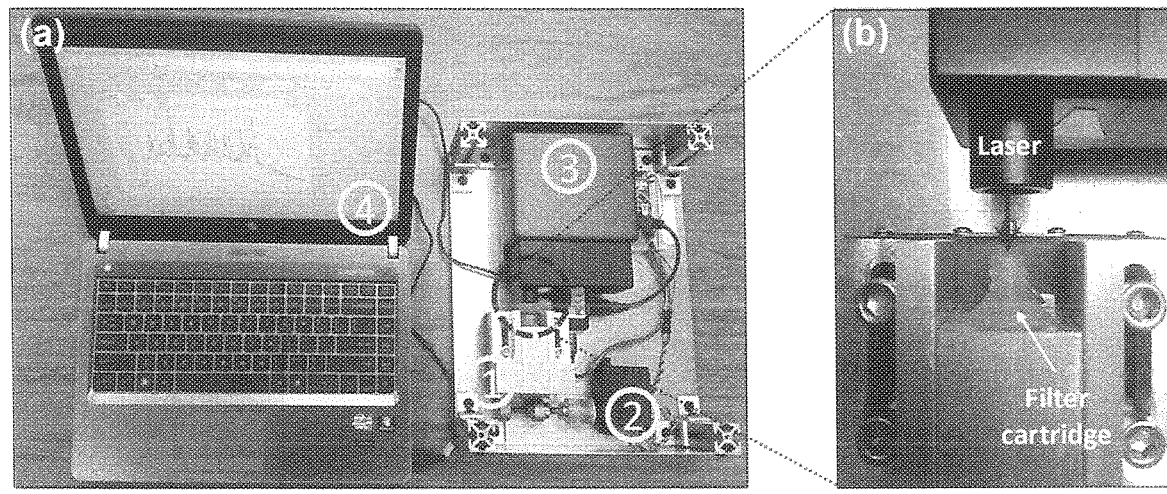
FIG. 7 illustrates (a) a layout of cost-efficient automated Raman device. It was mainly composed of a receptacle on a translation stage (1), a servo motor (2), a Raman system (3) and a laptop (4); (b) Custom filter cartridge was inserted for Raman spectroscopy.
Figure 12:
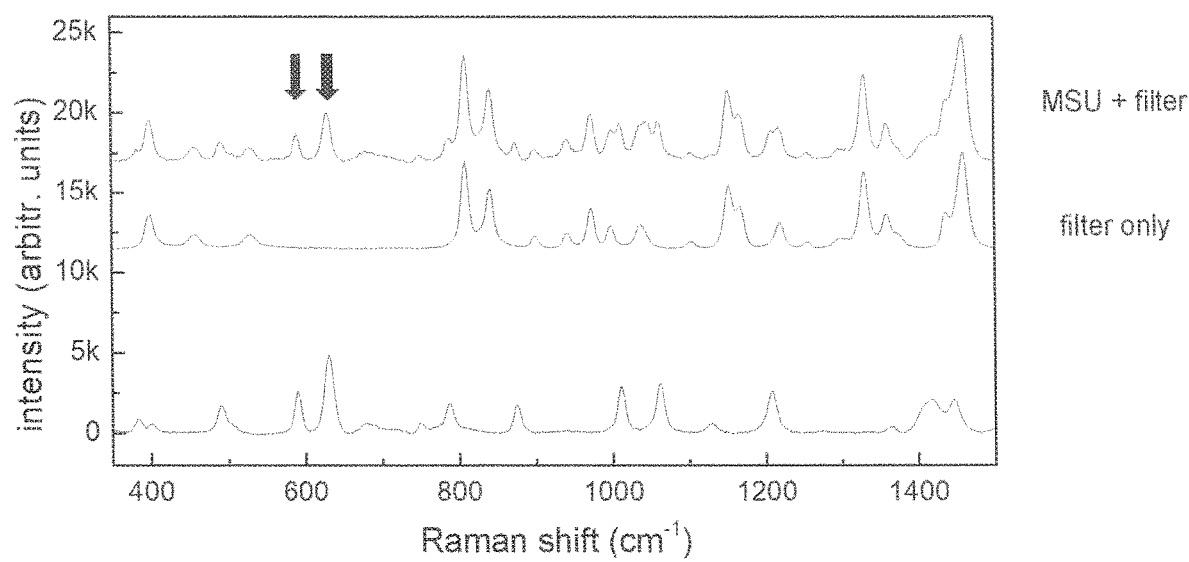
FIG. 12 illustrates representative Raman spectra of MSU crystals filter from a patient's synovial fluid (red), pure filter (black), the difference of previous two traces (green), and synthetic MSU crystals (blue) as a reference.

Background fluorescence was present at 785 nm wavelength, however, not to the extent of necessitating photobleaching. Raman spectra could be collected at short integration times (0.5 s) and high number of averages over a total duration of ~1 min (FIG. 12, red trace). The execution of data processing to remove background fluorescence and interfering filter related peaks was successful to the extent that all of the MSU related peaks were recovered (FIG. 12, green trace). While presence of all peaks is desirable, confirmation of the two major peaks at 590 and 631 cm-1 would be sufficient for diagnosis. In order to evaluate the performance of the low-cost Raman system, Raman spectra of the same samples were taken by using cost-efficient Raman system and scientific grade Raman system (FIG. 7).

Figure 8:
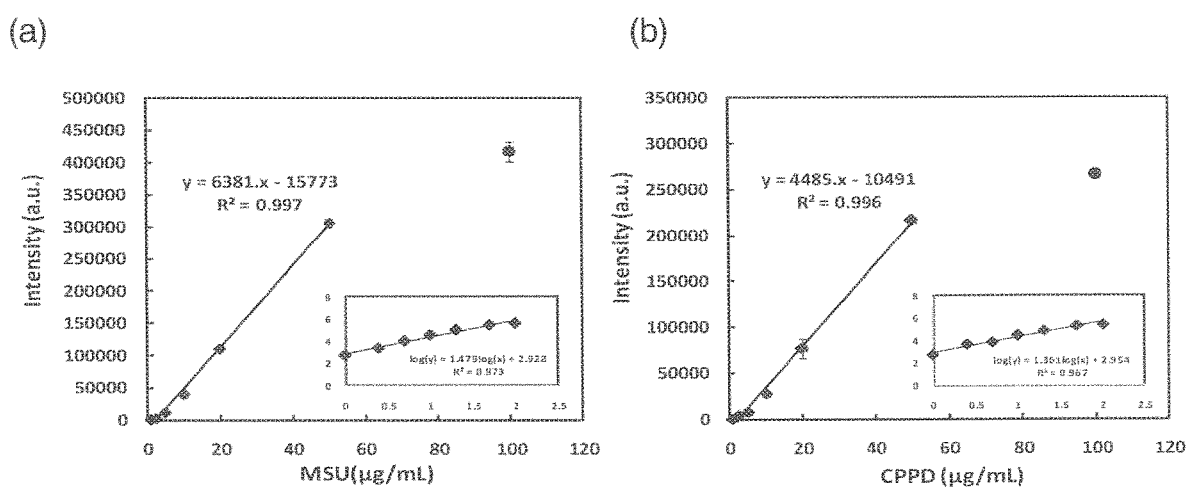
FIG. 8 (*a*) and (*b*) illustrate a 30-point Raman analysis which showed that the Raman intensity and crystal concentration were in a good linear relationship below the concentration of 50 μg/mL for both MSU and CPPD crystals, and above 50 μg/mL, the signal was gradually saturated. Samples which saturate the reading can be diluted and analyzed a second time to measure the amount of analyte within the volume.

The summation of the Raman signal intensities of the characteristic peaks (631 $cm^{-1}$ for MSU, 1050 $cm^{-1}$ for CPPD) was significantly and linearly related to the known crystal concentrations below the concentration at 50 µg/mL (for MSU, $R^2$=0.997; for CPPD, $R^2$=0.996). However, the Raman signal was gradually saturated above the concentration at 50 µg/mL (FIG. 8). Applying the 30-point scan, CARD was able to detect both MSU and CPPD crystals as low as 1 µg/mL.

Discussion

This work demonstrated the design and the feasibility of a cost-efficient automated Raman device (CARD) which was able to detect arthritic crystals (MSU and CPPD) in joint space, and the limit of detection of CARD was also studied. The digestion and filtration method was used to isolate crystals from clinical synovial aspirates and collect them over a submillimeter spot, helping to locate the crystals and improve the effect and efficiency of detection of crystals by Raman spectroscopy.

Hyaluronidase and Proteinase K were applied in sequence to digest the synovial fluid. Hyaluronidase was used to digest hyaluronic acid to reduce the viscosity of synovial fluid, and proteinase K dissolved organic debris to release intracellularly aggregated crystals. The digestion enabled the following filtration to collect crystals and remove the dissolved organic phase.

The simple and efficient sample preparation method reduced the treatment time to a practically acceptable level. A standard syringe filter holder was remodified for pushing digested synovial fluid and constricting the flow to go through a submillimeter spot to retain crystals on the filter membrane, while discarding the organic burden which further attenuated the fluorescence in Raman spectroscopy. After the crystals isolation by filtration, the custom filter cartridge could be directly placed at the laser focal plan, allowing to capture Raman spectra via the inlet port without having to remove the filter. An aluminum foil disc was applied to mask the scrambled background spectrum originating from the epoxy, which interfered with crystals associated peaks.

Raman mapping indicated that crystals were uniformly distributed within the submillimeter spot regardless of their concentrations, so that the method of scanning along the center diameter of the spot increased the fidelity for point-and-shoot Raman spectroscopy in the detection of crystals. A controlled servomotor was used to motorize the custom filter cartridge positioned on the translation stage at ~30 μm step, while the spectrometer was able to be synchronized with the motorization of the cartridge, making the data acquisition fully automated. Parameters, such as exposure time, average times and photobleaching session, could be configured in the LabVIEW program to achieve the optimized signal acquisition.

The rotational receptacle on the translation stage designed for insertion of the cartridge helped to deliver the cartridge into the CARD via the window, and meanwhile align the analyte to the laser beam. All components of CARD were able to be encapsulated into a 10"×12" light-tight footprint, promising a portable device for clinical application. No subjectivity got involved in the diagnosis by using CARD, outstripping the PLM-based diagnosis which is operator dependent. Others have proposed many approaches for detecting crystals in synovial fluid, but no one proposed similarly rapid and objective method.

At the concentration of 1 μg/mL, there were ~5 out of 30 spectra in which crystals associated peaks can be observed, no matter MSU or CPPD crystals, indicating that the detectable concentrations by using CARD was as low as 1 μg/mL for both MSU and CPPD crystals. This detectable concentration is significantly lower than the crystal concentrations (10~100 μg/mL) reported in clinical studies, which would improve the sensitivity and promise an early diagnosis. In CARD, crystals were collected over a small area, and as the concentration increased, the crystals would cover the overall area, resulting in the saturation of Raman signal at crystals associated peaks. However, based on the LOD study, the Raman signal intensity and crystal concentration were in a good linear relationship below the crystal concentration at 50 μg/mL. The standard deviations at all concentrations were small, verifying the uniform distribution of crystals over the well-defined area, which was also confirmed by Raman mapping. The limit of detection curve was able to be used as a reference criterion for estimating of the concentration of crystals, regardless of the saturation phenomenon.

Fluorescence background and filter background (interfering filter related peaks) had to be removed from the raw spectra to recover Raman signal of crystal associated peaks. The agreement between the processed spectrum of clinical MSU crystals (FIG. 12, green trace) and the reference spectrum of synthetic MSU crystals (FIG. 12, blue trace) indicated that for highly concentrated samples, most peaks were able to be sustained after the background correction. However, for samples with low crystal concentrations, some minor peaks cannot be retained after the correction. Nevertheless, the main MSU associated peaks at 631 $cm^{-1}$ and CPPD associated peaks at 1050 $cm^{-1}$ were sufficient for confirming the existence of crystals in this application.

Conclusion

A rapid, cost-efficient, and automated method for detection of crystals or particulates from biological fluids, such as those leading to joint arthropathies or urinary tract stones by Raman spectroscopy has been demonstrated. The cost-efficient and automated Raman device (CARD) including a practical sample preparation approach allows detection of clinically relevant concentration crystals or particulate in fluid using a low-cost Raman system. Clinically, samples are retrieved with a syringe by aspiration from joint space in some embodiments. Therefore, the utilization of syringe filter is very convenient and sample deposit is prepared essentially within minutes of the aspiration. The filter holder and filter are available commercially (e.g. Millipore) and our filter cartridge and method beneficially includes the described construction that restrains the flow to a smaller area, thereby, concentrating the analyte. The filtration device developed can be executed clinically in a disposable manner and at a minimal cost. The proposed approach to identification of crystal species is superior to the currently used polarized light microscopy and can increase acceptance of clinical synovial aspirate or kidney stone analysis more extensively, improving the unacceptably high misdiagnosis rate.

While in accordance with the patent statutes the best mode and preferred embodiment have been set forth, the scope of the invention is not limited thereto, but rather by the scope of the attached claims.

What is claimed is:

1. A filter cartridge for collecting crystals from a fluid, comprising:
   a) a filter holder having a base including an outlet and a top including an inlet;
   b) a condensing piece located within the filter holder and having an inlet and an outlet, with the outlet in fluid communication with the filter base;
   c) a filter membrane located between the condensing piece and the filter holder top, wherein the condensing piece channels flow of a fluid through the filter membrane such that a filtrate is collected at a location on the filter membrane that is smaller than a total surface area of the filter membrane; and
   d) an interference blocking disc located between the condensing piece and the filter membrane, wherein the disc includes an aperture that allows fluid to pass therethrough, and wherein the disc is a metal disc.

2. The filter cartridge according to claim 1, wherein the disc comprises aluminum and wherein the condensing piece comprises an epoxy casting.

3. The filter cartridge according to claim 2, wherein an o-ring is present in a fluid flow direction between the filter holder inlet and the filter membrane.

4. The filter cartridge according to claim 1, wherein the filter cartridge is designed such that the filtrate is placed on the filter membrane at a spot having a diameter less than 2 mm.

5. The filter cartridge according to claim 4, wherein the filter cartridge is designed such that the filtrate is placed on the filter membrane at a spot having a diameter less than 1 mm.

6. A method for determining if a particle or crystal is present in a sample of biological fluid, comprising the steps of:
   a) obtaining a sample of a biological fluid;
   b) filtering the biological fluid through the filter cartridge of claim 1, to recover particles or crystals in the filter cartridge;
   c) analyzing the crystals with a Raman spectroscopy device in a Raman system; and
   d) determining if the particles or the crystals are present, wherein the Raman system includes a receptacle adapted to receive the filter cartridge containing the filtrate.

7. The method according to claim 6, wherein the filter cartridge is placed in the receptacle such that the filtrate in the filter cartridge is located within 10 to 250 microns of a focal point of a laser of the Raman system.

8. The method according to claim 7, wherein the receptacle is mounted on a translation stage, and wherein the translation stage is moved from a first position to at least a second position in order to acquire spectra at different locations of a sample in order to increase an area of the filtrate surveyed.

9. The method according to claim 8, wherein a Raman spectrum acquired at each point is processed to remove fluorescence background and subtract any peaks related to the filtrate of the filter cartridge.

10. The method according to claim 6, wherein the biological fluid is blood, urine or synovial fluid.

* * * * *